United States Patent [19]

Schultz

[11] Patent Number: 4,766,891
[45] Date of Patent: Aug. 30, 1988

[54] ARTHROSCOPIC LEG HOLDER

[76] Inventor: James E. Schultz, 4476 Ampudia St., San Diego, Calif. 92103

[21] Appl. No.: 941,693

[22] Filed: Dec. 15, 1986

[51] Int. Cl.⁴ ............................................. A61F 3/00
[52] U.S. Cl. ................................. 128/133; 128/80 R
[58] Field of Search ................... 128/134, 133, 94, 99, 128/100, 80 R; 273/188, 189 R; 224/904, 149, 150

[56] References Cited

U.S. PATENT DOCUMENTS

| | | | |
|---|---|---|---|
| 1,806,601 | 5/1931 | Alexander | 128/134 |
| 1,845,338 | 2/1932 | Querna | 128/134 |
| 2,207,968 | 7/1940 | Brasure | 128/134 |
| 4,299,213 | 11/1981 | Violet | 128/133 |
| 4,373,709 | 2/1983 | Whitt | 269/328 |
| 4,407,277 | 10/1983 | Ellison | 128/82 |
| 4,457,302 | 7/1984 | Caspari et al. | 128/133 |
| 4,573,482 | 3/1986 | Williams, Jr. | 128/80 R |

FOREIGN PATENT DOCUMENTS 2100986 1/1983 United Kingdom ............... 128/133

Primary Examiner—Richard J. Johnson
Attorney, Agent, or Firm—Baker, Maxham & Jester

[57] ABSTRACT

A device to enable an arthroscopic surgeon to adjust the position of the lower leg with respect to the immobilized thigh portion of the leg as necessary during arthroscopic procedures. The device comprises a girdle around the surgeon's waist/hip area, having a stirrup on one or both sides. The stirrup retains the distal end of the leg, enabling the surgeon, with relatively minimal lateral and vertical hip motions, to adjust the area of interest in the knee for optimum access. The girdle is removably secured to the surgeon by a cinch strap having appropriate releasable securing means.

21 Claims, 2 Drawing Sheets

ARTHROSCOPIC LEG HOLDER

FIELD OF THE INVENTION

This invention relates generally to devices used in human diagnosis and surgery, and more particularly to a device encircling the waist of the surgeon and adapted to retain the lower end of a patient's leg to enable precise relative positioning of elements within the patient's knee.

DISCUSSION OF THE ART

The human knee is a very complex joint at the juxtaposed ends of the femur and tibia bones. Articular cartilage covers the ends of these bones, lateral and medial menisci cushions of cartilage are located between the facing bone ends, and ligaments and quadriceps muscles secure the joint together and give it stability and strength. The patella or kneecap also has articular cartilage on its underside.

Many activities prove to be too much for human knee joints. Sudden blows, falls or simple twists can result in knee injuries, particularly in the course of participating in athletics. Aging joints can cause trouble in older adults. Kneecap problems seem to be more prevalent in women. The cartilage and ligaments, referred to as soft tissues, inside the joint, are often damaged.

Diagnosing these problems internal to the complex knee joint has been greatly facilitated by the advent of arthroscopy. This relatively recent technique has enabled the orthopedic surgeon to obtain the necessary accurate diagnosis. Not only that, corrective surgery can often be performed arthroscopically, reducing surgical trauma and facilitating rapid recovery. Arthroscopy employs an arthroscope, a device based on fiber-optic technology. It requires tiny incisions, referred to as portals, through which the viewing arthroscope is inserted. Microsurgical instruments are inserted through such portals to trim or remove damaged tissue or to smooth roughened surfaces.

During arthroscopic diagnostic and surgical procedures, it is frequently necessary to adjust the relative position of the knee elements. Prior to commencement of the diagnosis or surgery, it is usually necessary to immobilize the thigh of the damaged leg with respect to the operating table. Representative apparatus for this purpose are shown in U.S. Pat. Nos. 4,299,213, 4,373,709 and 4,457,302. Typically, a surgical assistant then holds the lower leg and, pursuant to the operating surgeon's orders, raises or lowers or moves the lower leg portion laterally to enable the surgeon to see clearly the minute areas at which he is looking or in which he is also operating. Not only is it necessary for the leg to be moved in this way for his visual perception, but also for access of the instruments inserted in the portals.

The motions necessary to be produced by the assistant require applying considerable force to the knee joint. Knee operations often last for an hour or even longer, requiring an element of stamina on the part of the surgical assistant. Significant strength is also necessary because of the relative inelasticity of the ligaments supporting the knee joint. A relatively inexperienced assistant could create additional problems by not holding the leg steady enough to allow the surgeon to work expeditiously. Means to perform this assistant function mechanically is shown in U.S. Pat. No. 4,407,277. This device has restraining members for both the upper and lower leg portions which are movable with respect to each other. It has structure for applying lateral forces to the leg.

There are disadvantages in both the human and the mechanized leg positioning means. Both are only indirectly controlled by the operating surgeon. One responds in human manner, requiring frequent verbal ordering so that the joint relationships are just right for the particular procedure being conducted at any specific instant. This requires constant communication and teamwork, with human error always being a factor. The other, of course, is a mechanical device, which may be hydraulically controlled by the operating surgeon by means of a foot pedal. This is another example of an indirect or separate instrumentality making the actual changes in leg position. In both instances the surgeon has indirect control of leg positioning.

Although desirable, it has not previously been thought possible for the surgeon to directly position the knee joint at the precise time and in the precise location desired by moving the lower leg because both of his hands were fully involved in the surgical procedures.

SUMMARY OF THE INVENTION

It is a primary object of this invention to enable a surgeon, during a knee operation, to have direct control of positioning of the lower leg with respect to the immobilized thigh portion of the damaged knee. A very simple device is disclosed which does not have the drawbacks of mechanical means for accomplishing this purpose, nor does it have the drawbacks of a human assistant. Of course, it saves additional expense otherwise needed for the human assistant.

The device of this invention essentially comprises a relatively rigid girdle member with a cinch strap for removably securing it to the waist/hip area of the operating surgeon. On one or both opposite sides of the girdle, in the vicinity of the surgeon's hip, is a J-shaped stirrup member in which rests the lower leg of the patient. Typically the ankle area would rest in the stirrup.

By relatively minimal hip movements, given that the thigh is immobilized with respect to the operating table, the surgeon can directly and immediately with full and precise control, position the patient's lower leg to adjust the knee elements as desired during arthoscopic diagnosis and surgery.

BRIEF DESCRIPTION OF THE DRAWING

The objects, advantages and features of this invention will be more clearly understood from the following detailed description, when read in conjunction with the accompanying drawing, in which.

DESCRIPTION OF THE PREFERRED EMBODIMENT

Figure 1:
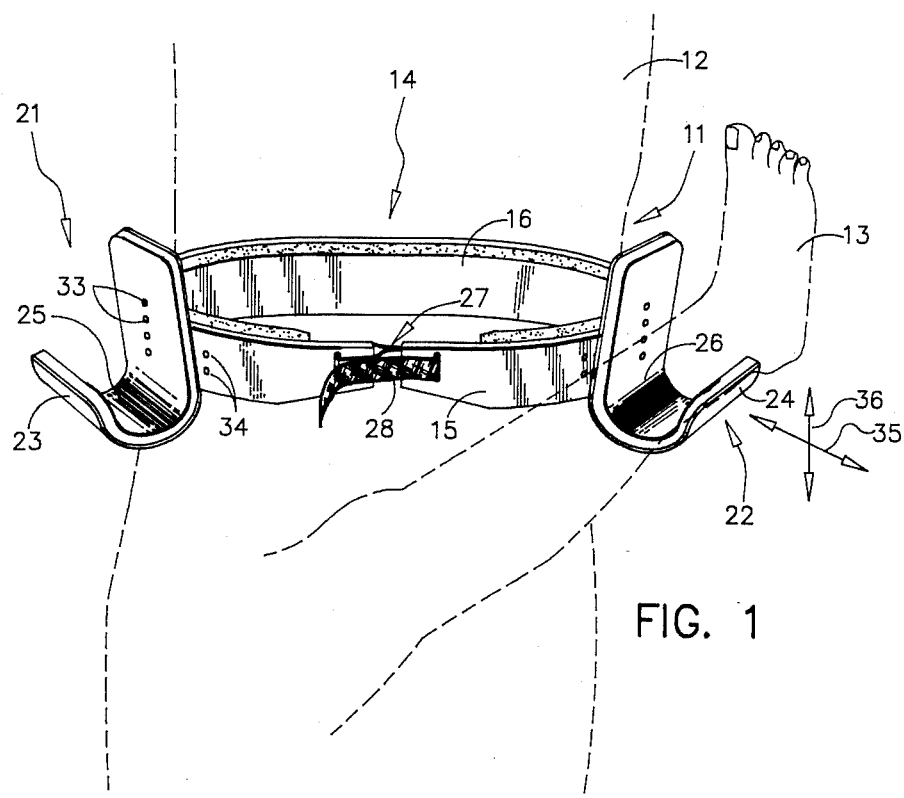
FIG. 1 is a perspective view of the leg holder of this invention as it would appear in relation to the operating surgeon and the leg on which the operation is being performed.

With reference now to the drawing, and more particularly to FIG. 1 thereof, there is shown leg holder apparatus 11 of the invention removably secured around the waist/hip area the surgeon, referred to by reference numeral 12. The lower portion 13 of the patient's leg is also shown in relation to the surgeon and the leg holder apparatus.

Figure 2:
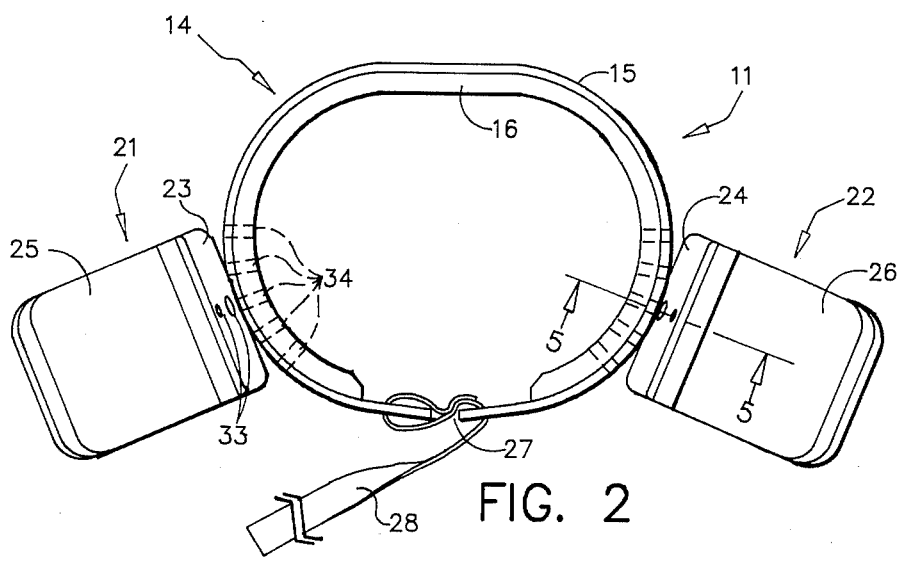
FIG. 2 is a top view of the apparatus of FIG. 1.
Figure 3:
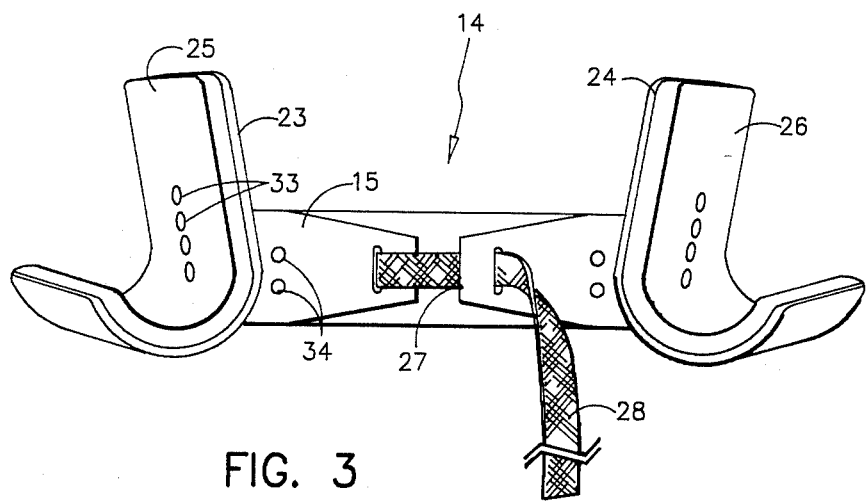
FIG. 3 is a front view of the apparatus of FIG. 1.
Figure 4:
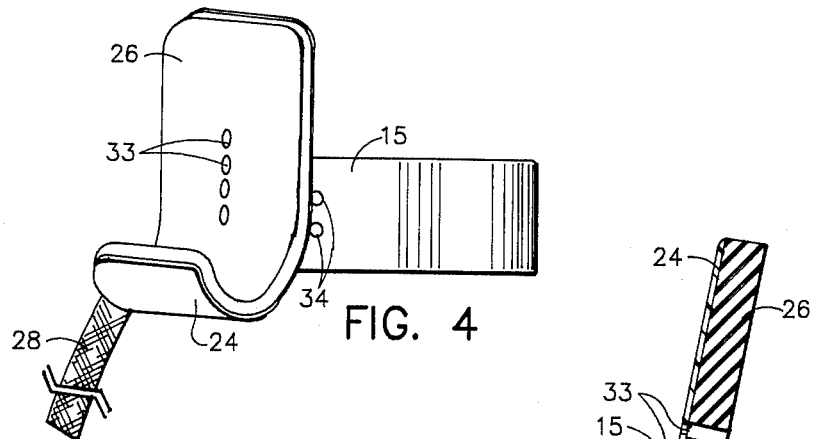
FIG. 4 is a side view of the invention from the right as viewed in FIG. 1.

The leg holder apparatus is comprised of girdle member 14 formed of shell element 15 and inner cushioning material 16. Stirrups 21 and 22 are J-shaped, also formed of shell members 23 and 24 and resilient cushioning members 25 and 26 respectively. The girdle is oval shaped, as seen particularly in FIG. 2, and has a separation 27, preferably in the front, which enables the relatively rigid girdle shell member to have some size flexibility and to allow it to open sufficiently to be placed around the surgeon's waist. The girdle is removably secured together by means of cinch strap 28 at the opening. This may be any type of tie or buckle arrangement or it may be a strap formed with mating hook and loop fabric fastener means enabling it to be easily released and the girdle removed from the operating surgeon.

Figure 5:
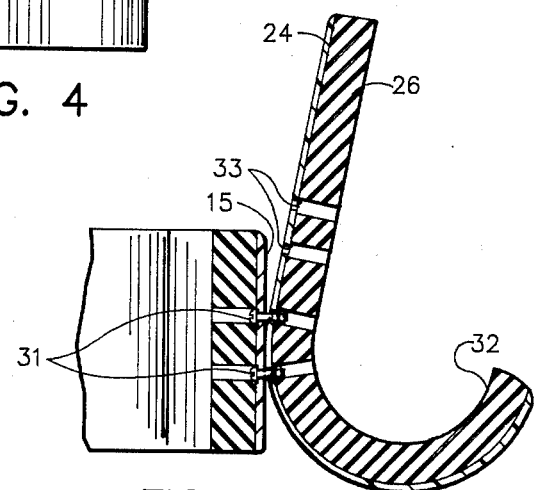
FIG. 5 is a partial sectional view taken through cutting plane 5—5 of FIG. 2.

The girdle and stirrup shell members are preferably formed of relatively rigid plastic material which, in the larger girdle member, permit the flexibility necessary to be placed on and taken off from the surgeon's torso. There is substantially no flexibility to the stirrups. The cushion material 16, 25 and 26 is typically sterilizable foam but it could be any other suitable material which provides the desired cushioning. The stirrups may be permanently secured to the girdle or they may be removably secured by means of bolts 31 as shown in FIG. 5. From this figure, and from the existence of additional holes 33 in the stirrups and holes 34 in the girdle member, it can be seen that the stirrup can be positioned as desired by the surgeon. In the arrangement shown in the drawing, the J-shaped stirrup is tilted slightly outward so that there is very little vertical lip 32. According to the surgeon's preference, the stirrup may be secured by means of bolts 31 through longitudinally spaced holes 33 thereby lowering the stirrup somewhat with respect to the girdle and making the stirrup more upright. This results in a more vertical outer lip 32. Also according to preference, the stirrup may be located farther forward or farther to the rear, by using different sets of circumferentially spaced holes 34 through girdle member 14.

Although the leg holder apparatus of the invention is shown with two stirrups, it could be just as effective with a single stirrup, again depending upon the preference of the surgeon. For example, the surgeon might want to have the stirrup on one side for left leg operations and have a separate leg holder with the stirrup on the other side for right leg operations. Other surgeons will want to have the freedom and flexibility of using either stirrup as necessary, depending upon the angle from which the damaged knee is approached or the side on which the procedures are to take place.

It can easily be appreciated from the above description and the drawing, that by simple and relatively small lateral movements of the surgeon's hips, lower leg 13 can be directly and precisely moved so as to change the relative position of the elements within the knee as necessary for proper arthroscopic procedures. This is referred to by double-headed arrow 35 in FIG. 1. Similarly, double-headed arrow 36 indicates that vertical motion can also be controlled directly by the surgeon.

Some of the advantages of this invention are that the surgeon has immediate, direct and precise control of the patient's lower leg positioning during arthroscopic procedures on the knee. Additionally one less surgical assistant is necessary during either diagnostic or surgical procedures. Further, there is no problem of holding the knee joint steady during the operation as might be the case with a human assistant. The strength and stamina of such an assistant is not a factor as it previously was, caused by the relatively high forces necessary to overcome some of the inelasticity of the knee joint.

While the invention has been described with respect to arthroscopic procedures on the knee of a human being, the device could be used for positioning other parts of the human body for similar or other procedures. For example, it could be used also on the arms, or it could be used on legs for medical purposes other than performing arthroscopic procedures. Thus, whenever the term "leg" is used in this specification and in the claims, it is understood to encompass arms. The term "arthroscopic procedures" is used for convenience herein and the invention is not limited to being used in conjunction with those procedures only.

It is likely that, in view of the above description, modifications and improvements to the invention will occur to those skilled in the art which are within the scope of the accompanying claims.

What is claimed is:

1. A device for assisting a surgeon during arthroscopic procedures, said device comprising:
   an oval-shaped substantially rigid girdle member adapted to embrace the waist/hip area of the surgeon, said girdle member having a separation to permit circumferential flexibility, said girdle member being formed with first and second opposite rounded sides and relatively flat front and back portions;
   a cinch strap connected to said girdle member across said separation to removably secure said girdle member around the surgeon; and
   substantially rigid leg holder means comprising at least one channel shaped, upwardly opening stirrup rigidly secured to said girdle member on at least one of said rounded sides thereof, said stirrup being adapted to receive and retain the lower leg portion of a patient during arthroscopic procedures;
   whereby when the patient's upper leg portion is immobilized the lower leg portion is controllably moved by the surgeon as necessary during arthroscopic procedures in both lateral and vertical directions.

2. The device recited in claim 1, wherein said leg holder means comprises one stirrup on each opposite rounded side of said girdle member, each said stirrup having a generally J-shape and being adapted to hold a patient's leg adjacent the distal end thereof.

3. The device recited in claim 1, wherein said separation forms juxtaposed ends to permit flexing and size adjustability, said cinch strap is removably secured to opposite said juxtaposed ends of said girdle member at the separation and is adjustably couplable to secure said girdle member around the surgeon.

4. The device recited in claim 1, and further comprising means to removably secure said stirrup to said girdle member.

5. The device recited in claim 4, wherein said securing means comprises at least one mating hole in each said stirrup and girdle member, bolt means extending through said mating holes, and a nut for engaging one end of said bolt means.

6. The device recited in claim 5, wherein said removable securing means further comprises additional holes through said stirrup, thereby permitting said stirrup to be secured to said girdle member at different relative positions and angles.

7. The device recited in claim 5, wherein said removable securing means further comprises additional holes through said girdle member circumferentially spaced from said mating hole, thereby permitting said stirrup to be located at different circumferential positions on said girdle member.

8. The device recited in claim 7, wherein said removable securing means further comprises additional holes through said stirrup, thereby permitting said stirrup to be secured to said girdle member at different relative positions and angles.

9. A device for assisting a surgeon during arthroscopic procedures, said device comprising:
an oval-shaped substantially rigid girdle member adapted to embrace the waist/hip area of the surgeon, said girdle member having a separation to permit circumferential flexibility, said girdle member being formed with first and second opposite rounded sides and relatively flat front and back portions;
a cinch strap connected to said girdle member across said separation to removably secure said girdle member around the surgeon;
substantially rigid leg holder means comprising at least one channel shaped, upwardly opening stirrup rigidly secured to said girdle member on at least one of said rounded sides thereof, said stirrup being adapted to receive and retain the lower leg portion of a patient during arthroscopic procedures; and
means for removably securing said stirrup to said girdle member;
whereby when the patient's upper leg portion is immobilized the lower leg portion is controllably moved by the surgeon as necessary during arthroscopic procedures in both lateral and vertical directions.

10. The device recited in claim 9, wherein said leg holder means comprises one stirrup on each opposite rounded side of said girdle member, each said stirrup having a generally J-shape and being adapted to hold a patient's leg adjacent the distal end thereof.

11. The device recited in claim 9, wherein said removable securing means comprises means for adjusting the position of said stirrup with respect to said girdle member.

12. The device recited in claim 11, wherein said position adjusting means comprises nut and bolt combinations and a plurality of holes through said girdle member and said stirrup, said holes through said girdle member being circumferentially spaced.

13. The device recited in claim 12, wherein said position adjusting means further comprises longitudinally spaced holes through said stirrup, thereby permitting said stirrup to be selectively positioned with respect to said girdle member.

14. A device for assisting a surgeon during arthroscopic procedures, said device comprising:
an oval-shaped substantially rigid girdle member adapted to embrace the waist/hip area of the surgeon, said girdle member having a separation to permit circumferential flexibility, said girdle member being formed with first and second opposite rounded sides and relatively flat front and back portions;
a cinch strap connected to said girdle member across said separation to removably secure said girdle member around the surgeon; and
substantially rigid leg holder means rigidly secured to said girdle member and comprising at least one channel shaped, upwardly opening stirrup, said stirrup being adapted to receive and retain the lower leg portion of a patient during arthroscopic procedures; and
means for removably securing said stirrup to said girdle member at a plurality of alternative circumferentially spaced locations on said girdle member and with selective orientations of said stirrup with respect to said girdle member;
whereby when the patient's upper leg portion is immobilized the lower leg portion is controllably moved by the surgeon as necessary during arthroscopic procedures in both lateral and vertical directions.

15. The device recited in claim 14, wherein said leg holder means comprises one stirrup on each opposite rounded side of said girdle member, each said stirrup having a generally J-shape and being adapted to hold a patient's leg adjacent the distal end thereof.

16. The device recited in claim 14 wherein:
said removable securing means comprises nut and bolt combinations and a plurality of longitudinally spaced holes through said stirrup and a plurality of circumferentially spaced holes through said girdle member;
whereby said stirrup may be raised or lowered and changed in orientation with respect to said girdle member and may be moved circumferentially with respect thereto.

17. A hands-free method for moving the leg of a patient by the operating surgeon during arthroscopic surgical procedures without the need for a human assistant, said method comprising the steps of:
immobilizing the patient's thigh with respect to the operating table on which the patient resides;
securing a substantially rigid, circumferentially adjustable girdle member around the surgeon's waist/hip area, the girdle member having at least one substantially rigid channel shaped upwardly opening stirrup rigidly secured on one side thereof;
placing the lower leg portion of the secured leg in the stirrup prior to commencement of the arthroscopic procedures; and then
moving the lower leg portion selectively laterally and vertically with respect to the immobilized thigh by appropriate movement by the surgeon to create necessary motion in the knee joint to enable the surgeon to gain appropriate access to the intricate aspects of the inner knee mechanism and the physiological elements therein.

18. The device recited in claim 17, wherein the stirrup is removably and adjustably secured to the girdle member, and comprising the further step of adjusting the position of the stirrup with respect to the girdle member prior to securing the girdle member around the surgeon.

19. A device for assisting a surgeon during arthroscopic procedures, said device comprising:
an oval-shaped substantially rigid girdle member adapted to embrace the waist/hip area of the surgeon, said girdle member having a separation to permit circumferential flexibility, said girdle member being formed with first and second opposite sides and front and back portions;
a cinch strap connected to said girdle member across said separation to removably secure said girdle member around the surgeon; and substantially rigid leg holder means comprising at least one channel shaped, upwardly opening stirrup rigidly secured to said girdle member on at least one of said sides thereof, said stirrup being adapted to receive and retain the lower leg portion of a patient during arthroscopic procedures;

whereby when the patient's upper leg portion is immobilized the lower leg portion is controllably moved by the surgeon as necessary during arthroscopic procedures in both lateral and vertical directions.

20. A device for assisting a surgeon during arthroscopic procedures, said device comprising:

an oval-shaped substantially rigid girdle member adapted to embrace the waist/hip area of the surgeon, said girdle member having a separation to permit circumferential flexibility, said girdle member being formed with first and second opposite sides and front and back portions;

a cinch strap connected to said girdle member across said separation to removably secure said girdle member around the surgeon;

substantially rigid leg holder means comprising at least one channel shaped, upwardly opening stirrup rigidly secured to said girdle member on at least one of said sides thereof, said stirrup being adapted to receive and retain the lower leg portion of a patient during arthroscopic procedures; and means for removably securing said stirrup to said girdle member;

whereby when the patient's upper leg portion is immobilized the lower leg portion is controllably moved by the surgeon as necessary during arthroscopic procedures in both lateral and vertical directions.

21. A device for assisting a surgeon during arthroscopic procedures, said device comprising:

an oval-shaped substantially rigid girdle member adapted to embrace the waist/hip area of the surgeon, said girdle member having a separation to permit circumferential flexibility, said girdle member being formed with first and second opposite rounded sides and relatively flat front and back portions;

a cinch strap connected to said girdle member across said separation to removably secure said girdle member around the surgeon; and substantially rigid leg holder means rigidly secured to said girdle member and comprising at least one channel shaped, upwardly opening stirrup, said stirrup being adapted to receive and retain the lower leg portion of a patient during arthroscopic procedures; and means for removably securing said stirrup to said girdle member at a plurality of alternative circumferentially spaced locations on said girdle member and with selective orientations of said stirrup with respect to said girdle member;

whereby when the patient's upper leg portion is immobilized the lower leg portion is controllably moved by the surgeon as necessary during arthroscopic procedures in both lateral and vertical directions.

* * * * *